United States Patent
Von Arx et al.

(10) Patent No.: US 7,335,161 B2
(45) Date of Patent: Feb. 26, 2008

(54) TECHNIQUES FOR BLOOD PRESSURE MEASUREMENT BY IMPLANTABLE DEVICE

(75) Inventors: Jeffrey A. Von Arx, Minneapolis, MN (US); Abhi Chavan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 245 days.

(21) Appl. No.: 10/922,816

(22) Filed: Aug. 20, 2004

(65) Prior Publication Data

US 2006/0041281 A1  Feb. 23, 2006

(51) Int. Cl.
*A61B 5/00* (2006.01)
(52) U.S. Cl. .......................... 600/485; 600/509; 607/17
(58) Field of Classification Search ................. 600/485, 600/509; 607/17–23
See application file for complete search history.

(56) References Cited

U.S. PATENT DOCUMENTS

| | | | |
|---|---|---|---|
| 3,995,623 A * | 12/1976 | Blake et al. ................. 600/381 |
| 5,040,536 A * | 8/1991 | Riff ............................. 607/23 |
| 5,368,040 A * | 11/1994 | Carney ........................ 600/513 |
| 5,564,434 A | 10/1996 | Halperin et al. |
| 5,700,283 A | 12/1997 | Salo |
| 5,987,352 A * | 11/1999 | Klein et al. .................. 600/509 |
| 6,277,078 B1 * | 8/2001 | Porat et al. .................. 600/486 |
| 7,097,618 B1 * | 8/2006 | Benditt et al. .............. 600/363 |
| 2003/0078506 A1 * | 4/2003 | Noren et al. ................. 600/485 |
| 2003/0191383 A1 | 10/2003 | Ben-Haim et al. |
| 2004/0078060 A1 | 4/2004 | Ding et a. |
| 2004/0106962 A1 | 6/2004 | Mai et al. |

FOREIGN PATENT DOCUMENTS

| | | |
|---|---|---|
| EP | 0985429 A2 | 3/2000 |
| WO | WO-2006023786 A2 | 3/2006 |

OTHER PUBLICATIONS

"International Search Report and Written Opinion for Application No. PCT/US2005/029643, date mailed Jun. 14, 2006", 16 Pages.
"Invitation to Pay Additional Fees and Partial Search Report for Application No. PCT/US2005/029643, date mailed Feb. 23, 2006", 8 Pages.

* cited by examiner

*Primary Examiner*—Charles A. Marmor, II
*Assistant Examiner*—Karen E. Toth
(74) *Attorney, Agent, or Firm*—Schwegman, Lundberg & Woessner, P.A.

(57) ABSTRACT

An implantable cardiac device is configured and programmed to collect blood pressure waveforms from one or more implantable pressure sensors. Techniques are described for extracting features and reducing noise in the pressure waveforms by averaging waveforms which are aligned with a detected cardiac cycle. Noise can also be reduced by gating and calibration functions performed in accordance with other sensor data.

8 Claims, 3 Drawing Sheets

TECHNIQUES FOR BLOOD PRESSURE MEASUREMENT BY IMPLANTABLE DEVICE

FIELD OF THE INVENTION

This present disclosure pertains to implantable medical devices such as implantable monitors, pacemakers, and cardioverter/defibrillators.

BACKGROUND

Cardiac failure refers to a condition in which the heart fails to pump enough blood to satisfy the needs of the body. It is usually due to some damage to the heart itself, such as from a myocardial infarction or heart attack. When heart failure occurs acutely, autonomic circulatory reflexes are activated that both increase the contractility of the heart, constrict the vasculature, and retain fluid as the body tries to defend against the drop in blood pressure. If the heart failure is not too severe, this compensation is enough to sustain the patient at a reduced activity level. Compensated heart failure, however, is a precarious state. If cardiac function worsens or increased cardiac output is required due to increased activity or illness, the compensation may not be able to maintain cardiac output at a level sufficient to maintain normal renal function. Fluid then continues to be retained, causing the progressive peripheral and pulmonary edema that characterizes overt congestive heart failure. Diastolic filling pressure becomes further elevated which causes the heart to become so dilated and edematous that its pumping function deteriorates even more. This condition, in which the heart failure continues to worsen, is decompensated heart failure. It can be detected clinically, principally from the resulting pulmonary congestion and dyspnea, and all clinicians know that it can lead to rapid death unless appropriate therapy is instituted.

DETAILED DESCRIPTION

It would be advantageous if there were a convenient means by which the decompensation status of a heart failure patient could be determined at an early stage. One way is to monitor one or more vascular pressures which either affect, or are affected by, the degree of heart failure in a patient. For example, left atrial pressure could be monitored since it becomes elevated with an increase in left ventricular dysfunction and may lead to pulmonary edema. Similarly, measurement of right atrial pressure provides an indication of the extent of right ventricular dysfunction. Measurement of systemic arterial pressure is also relevant since hypertension increases the afterload into which the heart must pump and may lead to further left ventricular dysfunction. The present disclosure relates to an implantable device which is configured with one or more intravascular pressure sensors for monitoring blood pressure at one or more sites. Blood pressure waveforms collected by an implantable sensor, however, can be noisy and have artifacts due to the patient's posture, body temperature, and activity level. Deriving clinically useful information from a blood pressure waveform may also depend upon the ability to relate certain features of the waveform to other physiological activity. Described herein are a number of different ways by which an implantable device, either alone or in conjunction with one or more external devices, may use other sensing modalities in order to identify features and reduce the noise in blood pressure waveforms.

Figure 1:
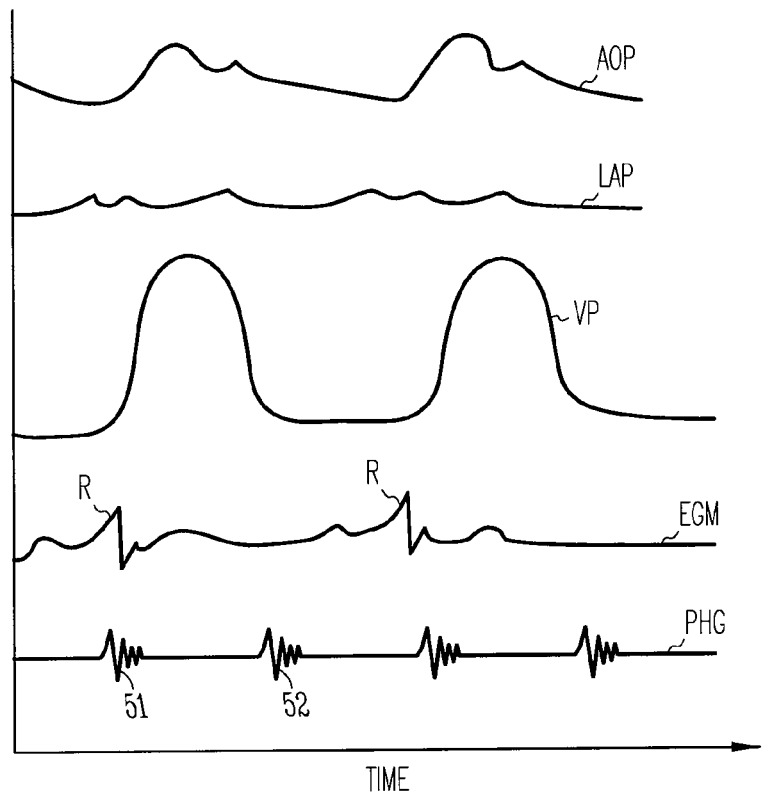
FIG. 1 illustrates exemplary blood pressure waveforms collected during two cardiac cycles.

Clinically useful features may be identified in a blood pressure waveform if the time course of the waveform is related with simultaneously occurring cardiac activity. The cardiac sensing capability of an implantable cardiac device may be used for this purpose by using chamber senses derived from electrogram signals or delivered paces to mark the time at which a heart beat starts. Alternatively, a phonocardiogram generated by an implantable microphone may be used to detect cardiac activity. Blood pressure waveforms may then be collected as digitized sample values, where the time at which each sample value is collected is made the same with respect to a detected heart beat among the collected waveforms. Alignment of the collected pressure waveforms with the cardiac cycle can be done by simultaneously sampling and storing the blood pressure waveforms and the cardiac activity signals with time stamps. FIG. 1 shows an example of an aortic pressure waveform AOP, a left atrial pressure waveform LAP, and a left ventricular pressure waveform VP over two successive cardiac cycles. For each such waveform, samples can be collected and aligned with the cardiac cycle as marked by either an r-wave R from the electrogram signal EGM or a heart sound S1 or S2 from the phonocardiogram PHG. Such alignment of a blood pressure waveform with detected cardiac activity allows the extraction of clinically useful information such as end-diastolic pressure.

Alignment of a plurality of collected blood pressure waveforms with the cardiac cycle also allows further processing to be performed to reduce noise and artifact. For example, if a gap occurs in a pressure waveform due to signal loss during its collection, the information may be filled in with the corresponding part of another collected pressure waveform which is aligned at the same time with respect to the cardiac cycle as the gap. Such signal loss may be particularly prone to occur with pressure sensors which transmit their signals wirelessly as described below. Alignment of collected blood pressure waveforms with cardiac activity also allows noise to be reduced through signal averaging. A standard technique for reducing noise in a signal is to collect a number of such signals at different times and under similar conditions and then average the collected signals. Such averaging serves to cancel out noise due to factors which cause a random variation in the signal, leaving only the systemic or true variation. Blood pressure waveforms generated by an implantable pressure sensor are subject to such random variation due to, for example, body movement while the blood pressure waveform is being collected. In order to perform averaging of blood pressure waveforms, however, the systemic variation in the waveform needs to be constant from waveform to waveform. A way of providing this constant systemic variation is to align the collected blood pressure waveforms with the cardiac cycle as described above prior to averaging. Beat to beat averaging of the pressure waveforms can then be done using features (e.g., chamber senses or heart sounds) detected from the cardiac activity signal as markers for alignment of successive pressure waveforms.

Noise can also be removed from a blood pressure waveform by only collecting such waveforms when specified conditions are known to exist which result in less artifact being present in the signal. Such windowing or gating of blood pressure measurement may be performed in accordance with information received from other sensing modalities with which the implantable device is equipped. For example, a patient's physical activity has a significant effect on a blood pressure waveform. An activity level signal such as provided by an accelerometer may therefore be used to gate blood pressure measurements so that pressure waveforms are collected only during periods of relative inactivity. A patient's posture also affects a blood pressure waveform due to hydrostatic effects. A spatial orientation signal from a posture sensor may be used to gate blood pressure measurements so that pressure waveforms are collected only during periods when the patient is in one or more specific postures (e.g., lying down). Also, virtually all pressure sensors are also affected by temperature variation. A temperature sensor may therefore be used to gate blood pressure measurements so that pressure waveforms are collected only when the patient's body temperature is in a specified range. Similar gating functions may be performed in accordance with other data such as detected heart rate and exertion level.

Information derived from other sensing modalities can also be used to reduce noise in a blood pressure waveform by calibrating the waveform in accordance with the information. For example, the spatial orientation signal from a posture sensor can be used to calibrate a collected pressure waveform to take into account the hydrostatic effects of the patient's posture. A collected pressure waveform may also be calibrated with a temperature signal using the known temperature variation of the pressure sensor. Such calibration functions may be performed alone or in conjunction with the gating functions described above.

1. Exemplary Implantable Device Description

Collection of blood pressure waveforms as described above may be implemented in any type of cardiac device (e.g., a conventional pacemaker, resynchronization pacemaker, defibrillator, combination device, or heart monitor) having the necessary sensing capabilities for measuring blood pressure and cardiac activity. Described below is an implantable cardiac rhythm management device which may be programmed to collect the needed data for blood pressure measurement and noise reduction.

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be used to treat heart failure patients suffering from ventricular conduction disorders by pacing both ventricles in order to result in a more coordinated contraction, termed cardiac resynchronization therapy.

Figure 2:
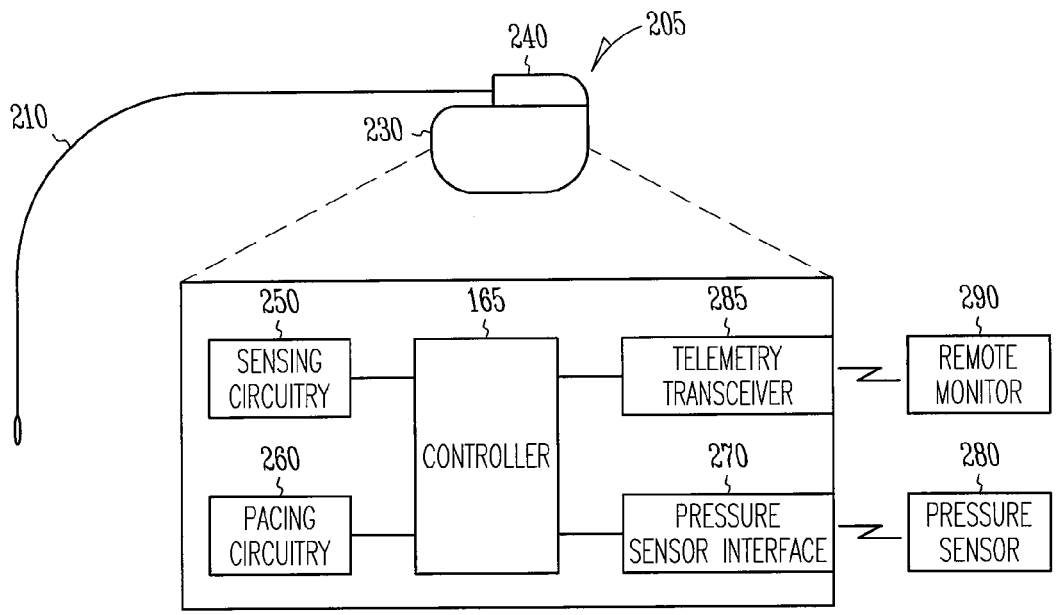
FIG. 2 illustrates an exemplary implantable cardiac device.

Cardiac rhythm management devices are contained within a housing which is usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. FIG. 2 illustrates an implantable device 205 and a lead 210 having electrodes incorporated therein for disposition in the right atrium or ventricle or in a cardiac vein for sensing cardiac activity and/or delivering electrical stimulation to the heart. The device 205 includes a hermetically sealed housing 230, formed from a conductive metal, such as titanium. A header 240, which may be formed of an insulating material, is mounted on housing 230 for receiving leads such as lead 210 or other leads used for cardiac sensing or stimulation. Contained within the housing 230 is electronic circuitry interfaced to the controller 165 and connected to one or more leads for providing pacing functionality to the device, including sensing circuitry 250 and pacing circuitry 260. A telemetry transceiver 285 enables the controller to communicate with a remote monitor 290 or external programmer via a wireless link. In order to perform the blood pressure sensing function, one or more pressure sensors are also interfaced to the controller. Shown in the figure is a pressure sensor interface 270 which receives pressure signals produced by an implantable pressure sensor 280. The pressure sensor 280 may be incorporated in an intravascular lead such as lead 210 which may be disposed within the heart or a blood vessel or may be a separately implantable satellite unit which communicates wirelessly with the controller. In the latter case, the sensor 280 may be incorporated into a vascular stent and includes both a blood pressure sensor and a telemetry transmitter for transmitting the blood pressure waveform to the device 205. The pressure sensor interface 270 in that case functions as a wireless telemetry receiver. A flow sensor may be similarly incorporated into a wireless satellite unit.

A system-level diagram of an exemplary implantable cardiac rhythm management device such as that described above is shown in FIG. 3. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. The telemetry transceiver 285 enables the controller to communicate with an external device 90 via a wireless telemetry link. The external device 90 may be an external programmer which can be used to program the implantable device as well as receive data from it or a remote monitoring unit. The external device 90 may also be interfaced to a patient management network 91 enabling the implantable device to transmit data and alarm messages to clinical personnel over the network. The network connection between the external device 90 and the patient management network 91 may be implemented by, for example, an internet connection, over a phone line, or via a cellular wireless link.

Figure 3:
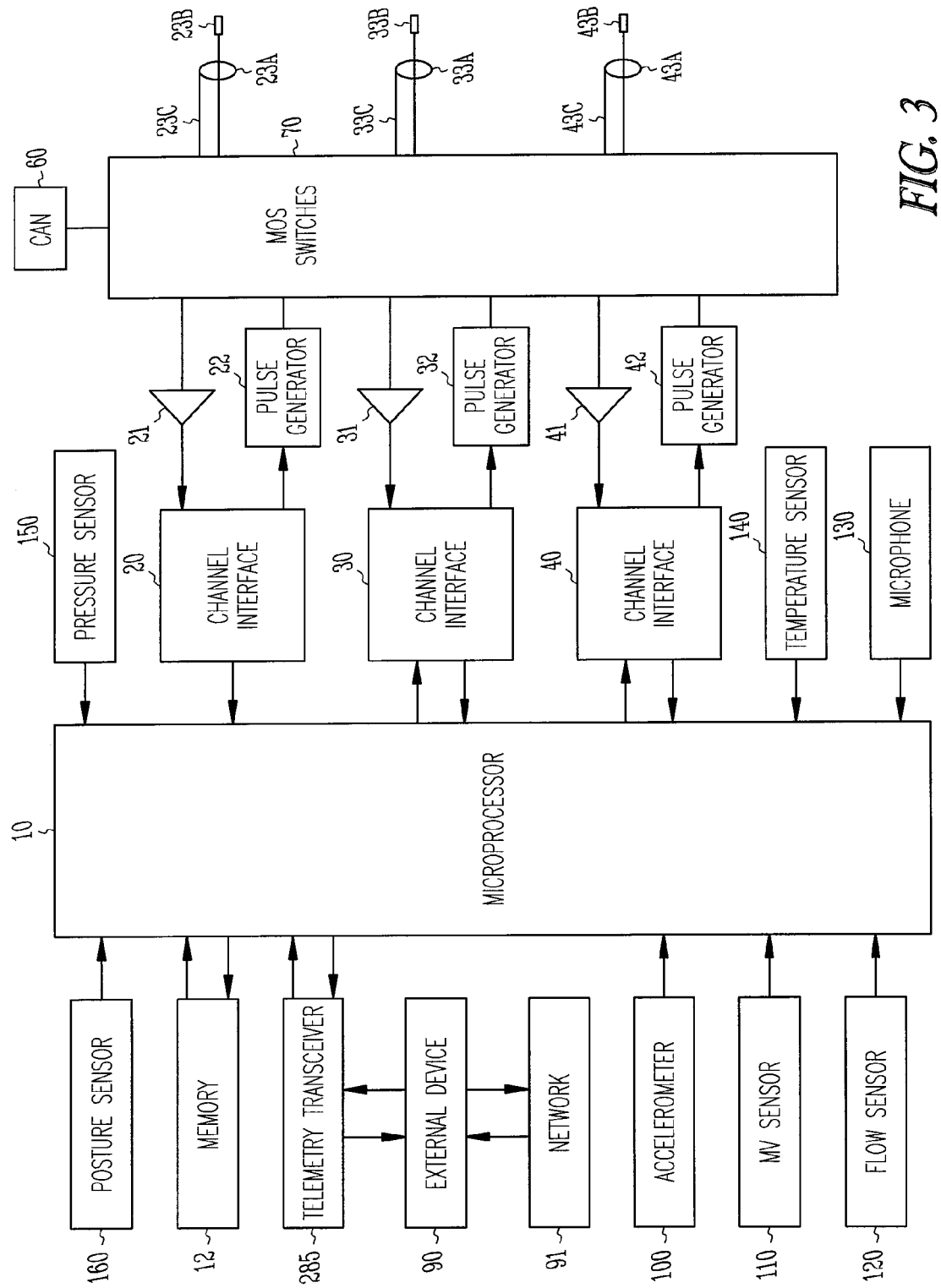
FIG. 3 is a system diagram of an exemplary cardiac rhythm management device.

The embodiment shown in FIG. 3 has three sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. A sensing/pacing channel may include ring electrode 43a (33a or 23a) and tip electrode 43b (33b or 23b) of bipolar lead 43c (33c or 23c), sense amplifier 41 (31 or 21), pulse generator 42 (32 or 22), and a channel interface 40 (30 or 20). The channels may be configured as either atrial or ventricular channels. For example, the device may be configured for atrial pacing and either single ventricle or biventricular (resynchronization) pacing. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator (not shown) may also be interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates chamber sense signals (i.e., atrial or ventricular senses, also referred to as p-waves and r-waves, respectively) when voltages sensed by the electrodes of a particular channel exceed a specified threshold. The controller 10 interprets sense signals from the sensing channels in order to detect arrhythmias and to control the delivery of paces in accordance with a pacing algorithm that employs such senses to trigger or inhibit pacing. Most pacing modes are so-called demand modes where a heart chamber is paced upon expiration of an escape interval without receipt of a sense from that chamber. For example, in an atrial triggered mode, an atrial sense initiates an AV escape interval so that one or both ventricles are then paced upon expiration of the interval if no intrinsic ventricular activity occurs beforehand. The ventricles may also be paced upon expiration of an escape interval initiated by a ventricular sense or pace, and the atria may be paced by a ventriculo-atrial escape interval initiated by a ventricular sense or pace. As described herein, the electrogram signals generated by a sensing channel can be used to detect cardiac activity for aligning collected blood pressure waveforms prior to averaging. Alternatively, cardiac activity can be detected via a phonocardiogram generated by a microphone 130.

Also interfaced to the controller are a minute ventilation sensor 110 and an accelerometer 100 for use in measuring a parameter related to the patient's exertion level and adjusting the pacing rate of the device accordingly in rate-adaptive pacing modes. The accelerometer and minute ventilation sensor produce a signal which approximates the patient's exertion level by measuring body activity and respiratory volume rate, respectively. The minute ventilation sensor measures the respiratory volume by injecting bursts of excitation current between excitation electrodes and measuring a transthoracic voltage drop to derive a signal proportional to the transthoracic impedance. (A particular minute ventilation sensor is described in U.S. Pat. No. 6,161,042, assigned to the assignee of the present application and hereby incorporated by reference in its entirety.) In a rate-adaptive pacing mode, one or more escape intervals are adjusted in accordance with a measured exertion level so that the pacing rate varies with metabolic demand. The modified pacing rate dictated by a rate-adaptive algorithm is referred to as the sensor-indicated rate. The rate-adaptive algorithm calculates the sensor-indicated rate by mapping a measured exertion level to a heart rate in accordance with a function referred to as the response factor. As described earlier, signals from the accelerometer and minute ventilation sensors may also be used to gate the collection of blood pressure waveforms.

One or more implantable pressure sensors 150 are interfaced to the controller to enable the collection of blood pressure waveforms. As described above, the pressure sensors may be either incorporated into intravascular leads or may be wireless satellite units. Other sensors interfaced to controller for providing signals used to gate or calibrate collected blood pressure waveforms include a temperature sensor 140 and a posture sensor 160. In one embodiment, the posture sensor is a multi-axis accelerometer which allows the controller to compute the patient's posture from measured accelerations along the multiple axes.

A flow sensor 120 is also provided for generating a signal indicative of blood flow. If a blood pressure waveform and a flow waveform are generated simultaneously from sensors located near one another in the same blood vessel, the controller is able to compute a downstream flow resistance value.

2. Exemplary Implementation

There are many ways in which an implantable device may implement and use the techniques for collecting blood pressure waveforms with noise reduction as described above. For example, blood pressure waveforms may be collected by the device and stored with time stamps or other means for aligning the waveforms with detected cardiac activity. Averaging of the waveforms and/or other processing such as feature extraction may then be performed by the implantable device or an external device such as an external programmer to which the collected waveforms are downloaded. Similarly, other sensing data such as heart rate, activity level, posture, and temperature may be stored with collected pressure waveforms and then used by the implantable device or an external device to calibrate the waveforms as described above. Sensing data such as heart rate, activity level, posture, and temperature may also be used by the implantable device to gate when pressure waveforms are collected, or the data may be used by an external device or a clinician to which the data is presented in order to determine which of a plurality of collected pressure waveforms should be selected for further processing or analysis.

Figure 4:
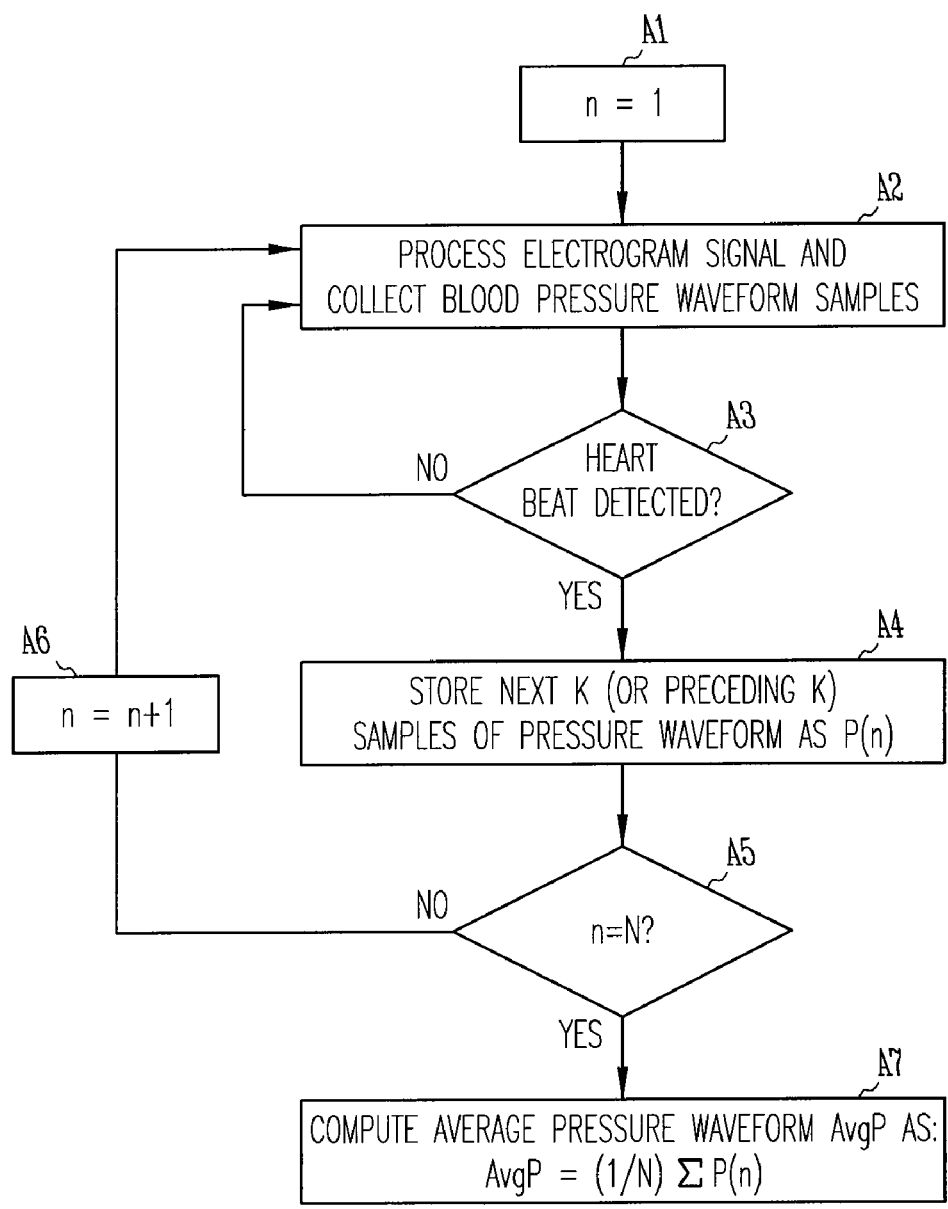
FIG. 4 illustrates an exemplary algorithm for blood pressure waveform averaging.

Illustrated in FIG. 4 is one particular exemplary algorithm which could be implemented in an implantable cardiac rhythm management device by appropriate programming of the device controller and/or programming of an external device to which data is downloaded from the implantable device. The algorithm generates an average pressure waveform AvgP which is made up of K sample values, where K is a specified integer. Each of the K sample values of AvgP is an average of the corresponding samples of N pressure waveforms collected from the pressure sensor during N heart beats, where N is a specified integer. The algorithm begins at step A1 where an index counter n is initialized to 1. At step A2, an electrogram is collected by the device, either as samples or in analog form, in order to detect intrinsic cardiac activity. Concurrently with the collection of the electrogram, pressure waveform samples are also collected from the pressure sensor. At step A3, the device detects whether a heart beat has occurred by either detecting intrinsic cardiac activity in the electogram or determining that a pace has been delivered. The detected heart beat may be either an atrial beat as detected from a p-wave in the electrogram or delivery of an atrial pace, or a ventricular beat as detected from an r-wave in the electrogram or delivery of a ventricular pace. In an alternate embodiment, a phonocardiogram produced by a microphone may be used to detect intrinsic cardiac activity. In that case, the first heart sound S1 is produced by AV valve closure and indicates the start of ventricular systole, while the second heart sound S2 is produced by pulmonary and aortic valve closure indicating the start of ventricular diastole. If a heart beat has occurred, a pressure waveform made up of K number of pressure waveform samples is stored in a buffer as P(n) at step A4. The K pressure waveform samples of P(n) may be aligned with the heart beat in one of two different ways so that P(n) contains either the next K pressure samples after detection of the heart beat or the K pressure samples preceding detection of the heart beat. If the measured pressure is an arterial pressure, it may be desirable for the pressure waveform P(n) to start with the beginning of systole so that the first sample of P(n) coincides with the detected heart beat. If the measured pressure is a left atrial or other venous pressure, on the other hand, it may be desirable for the pressure waveform P(n) to start with the beginning of diastole so that the last sample of P(n) coincides with detection of the heart beat. In the latter case, pressure waveform samples may be stored in a rolling or FIFO buffer at step A2 so that the buffer will contain the preceding K pressure samples after detection of a heart beat. At step A5, the index counter n is tested to see if N pressure waveforms have been collected. If not, the index counter is incremented at step A6 and the algorithm returns to step S2 for collection of another waveform. If N pressure waveforms have been collected, an average waveform AvgP is computed at step A7 as:

$$AvgP = (1/N)\Sigma P(n)$$

where the summation is carried out from n=1 to N by summing the corresponding K samples of each pressure waveform P(n). Any desired number of average waveforms AvgP may be computed in the manner just described. The algorithm may also be executed at any desired time such as periodically according to a schedule, upon receiving a command from an external programmer, or upon detection of a specific event or condition. The average waveform(s) may then be transmitted to an external programmer or other external device for graphical or numerical display to a clinician.

The implantable device may collect other data which may be used to reduce noise and/or remove artifacts in collected pressure waveforms by either calibrating the waveforms or gating when the waveforms are collected. Such gating or calibration techniques may be used in collecting pressure waveforms whether or not the collected waveforms are averaged as described above. In the gating technique, the collection of pressure waveforms is performed only when a particular condition or conditions are present. For example, a pressure waveform is collected only if the heart rate as measured by the interval between r-waves or p-waves (or paces) is within a specified range, if the exertion level as measured by an activity level sensor (e.g., an accelerometer) or minute ventilation sensor is within a specified range, if the temperature signal from a temperature sensor indicates the patient's body temperature is within a specified range, or if the spatial orientation signal from a posture sensor indicates the patient is in one or more specific postures. In the calibration technique, the samples of a collected pressure waveform are modified in order to compensate for the effects of conditions indicated by sensor data. For example, the pressure waveform samples may be calibrated with a temperature signal and/or a spatial orientation signal in order to compensate for the effects of the patient's temperature or posture on the blood pressure waveform. Data such as heart rate, activity level, posture, and temperature may also be stored along with collected pressure waveforms which information can then be displayed in graphical or numerical form to a clinician for analysis.

Either the implantable device or an external device may also be programmed to analyze collected blood pressure waveforms, either after averaging or not, and extract features therefrom which can be compared with alarm limit values. For example, peak left atrial pressure or left ventricular pressure values may be extracted and compared with a limit value so that an alarm flag may be set to alert-clinical personnel if the pressure is high. The implantable or external device may also be programmed to calculate a vascular resistance value by dividing a peak pressure value by a corresponding peak flow value. For example, the device may be interfaced to pressure and flow sensors located in the aorta so that division of peak pressure by peak flow represents an estimate of the patient's total peripheral resistance. An implantable or external device may also be programmed to use features extracted from pressure waveforms such as peak pressure or maximum change in pressure dP/dt to automatically adjust pacing parameters such as the AV delay or length of other escape intervals, biventricular offset interval, or rate adaptive pacing parameters. Features extracted from pressure waveforms may also useful for cardiac rhythm discrimination in some instances.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A device, comprising:
   a sensing channel for generating signals reflective of cardiac electrical activity;
   an intravascular pressure sensor for generating blood pressure waveforms;

a controller interfaced to the sensing channel and the intravascular pressure sensor; and, wherein the controller is programmed to collect a plurality of blood pressure waveforms as digitized sample values, align the collected waveforms by making the time at which each corresponding sample value is collected the same with respect to detected cardiac electrical activity among the collected waveforms, and compute an average blood pressure waveform by averaging corresponding samples of the collected waveforms.

2. The device of claim 1 further comprising:

a posture sensor interfaced to the controller for generating a spatial orientation signal indicative of the patient's posture; and, wherein the controller is programmed to calibrate the pressure waveforms in accordance with the spatial orientation signal in order to compensate for the effects of the patient's posture on the blood pressure waveforms.

3. The device of claim 1 further comprising:

a posture sensor interfaced to the controller for generating a spatial orientation signal indicative of the patient's posture; and, wherein the controller is programmed to collect pressure waveforms only when the spatial orientation signal indicates the patient is in one or more specific postures.

4. The device of claim 1 wherein the controller is programmed to align the collected blood pressure waveforms by simultaneously sampling and storing the blood pressure waveforms and the cardiac electrical activity signals with time stamps.

5. A method, comprising:

generating signals reflective of cardiac electrical activity;

generating blood pressure waveforms from an intravascular location;

collecting a plurality of blood pressure waveforms as digitized sample values and aligning the collected waveforms by making the time at which each corresponding sample value is collected the same with respect to detected cardiac electrical activity among the collected waveforms; and, compute an average blood pressure waveform by averaging corresponding samples of the collected waveforms.

6. The method of claim 5 further comprising:

generating a spatial orientation signal indicative of the patient's posture; and, collecting pressure waveforms for averaging only when the spatial orientation signal indicates the patient is in one or more specific postures.

7. The method of claim 5 further comprising downloading the collected and aligned pressure waveforms from an implantable device to an external device, wherein the averaging of the pressure waveforms is performed by the external device.

8. The method of claim 5 further comprising:

generating a spatial orientation signal indicative of the patient's posture; and, calibrating the pressure waveforms before averaging in accordance with the spatial orientation signal in order to compensate for the effects of the patient's posture on the blood pressure waveforms.

* * * * *

UNITED STATES PATENT AND TRADEMARK OFFICE
CERTIFICATE OF CORRECTION

PATENT NO. : 7,335,161 B2
APPLICATION NO. : 10/922816
DATED : February 26, 2008
INVENTOR(S) : J. Von Arx et al.

It is certified that error appears in the above-identified patent and that said Letters Patent is hereby corrected as shown below:

On the Title page, in field (56), under "U.S. Patent Documents", in column 2, line 6, delete "Ding et a." and insert -- Ding et al. --, therefor.

Signed and Sealed this

First Day of July, 2008

JON W. DUDAS
*Director of the United States Patent and Trademark Office*